(12) United States Patent
Dooley et al.

(10) Patent No.: US 7,799,234 B2
(45) Date of Patent: Sep. 21, 2010

(54) IN-LINE WASTE DISINFECTION METHOD

(75) Inventors: Joseph B. Dooley, Kingston, TN (US); Jeffrey G. Hubrig, Knoxville, TN (US); Richard A. Lowden, Clinton, TN (US)

(73) Assignee: Innovation Services, Inc., Knoxville, TN (US)

( * ) Notice: Subject to any disclaimer, the term of this patent is extended or adjusted under 35 U.S.C. 154(b) by 656 days.

(21) Appl. No.: 11/697,933

(22) Filed: Apr. 9, 2007

(65) Prior Publication Data

US 2008/0245744 A1 Oct. 9, 2008

(51) Int. Cl.
*C02F 1/50* (2006.01)
*C02F 1/72* (2006.01)

(52) U.S. Cl. .................. 210/752; 205/742; 205/756; 210/748.18; 210/754; 210/756; 210/758; 210/759; 210/760; 210/764; 210/765

(58) Field of Classification Search .............. 210/758
See application file for complete search history.

(56) References Cited

U.S. PATENT DOCUMENTS

| | | | |
|---|---|---|---|
| 2,243,761 A | 5/1941 | Matzka | |
| 2,658,033 A | 11/1953 | Ferris | |
| 2,687,996 A | 8/1954 | Butler | |
| 3,703,453 A * | 11/1972 | Gordy et al. | 588/303 |
| 3,864,258 A | 2/1975 | Richardson et al. | |
| 3,925,176 A * | 12/1975 | Okert | 205/701 |
| 4,054,139 A | 10/1977 | Crossley | |
| 4,192,742 A | 3/1980 | Bernard et al. | |
| 4,197,347 A * | 4/1980 | Ogawa et al. | 428/328 |
| 4,492,618 A | 1/1985 | Eder | |
| 4,680,114 A | 7/1987 | Hayes | |
| 4,741,831 A * | 5/1988 | Grinstead | 210/638 |
| 4,783,246 A | 11/1988 | Langeland et al. | |
| 4,935,116 A | 6/1990 | LeMire | |
| 4,992,213 A * | 2/1991 | Mallett et al. | 510/427 |
| 5,059,296 A | 10/1991 | Sherman | |
| 5,073,298 A * | 12/1991 | Gentle et al. | 516/117 |
| 5,073,382 A | 12/1991 | Antelman | |
| 5,077,007 A * | 12/1991 | Pearson | 422/3 |
| 5,078,902 A | 1/1992 | Antelman | |
| 5,085,753 A | 2/1992 | Sherman | |
| 5,087,370 A * | 2/1992 | Schultheis et al. | 210/638 |
| 5,094,739 A | 3/1992 | Kump | |

(Continued)

FOREIGN PATENT DOCUMENTS

| | | |
|---|---|---|
| DE | 10009643 | 9/2001 |
| GB | 384466 | 12/1932 |
| GB | 1400215 | 7/1975 |
| GB | 2298858 | 9/1996 |
| JP | 11235597 | 8/1999 |
| WO | 9918790 | 4/1999 |
| WO | 0236499 | 5/2002 |

OTHER PUBLICATIONS

I.B. Romans, Oligodynamic Metals, Disinfection, Sterilization, and Preservation, 1968, Chapter 24, 372-400, Lea & Febiger, Philadelphia.

(Continued)

*Primary Examiner*—Peter A Hruskoci
(74) *Attorney, Agent, or Firm*—Luedeka, Neely & Graham, P.C.

(57) ABSTRACT

A modular waste disinfection system for the disinfection of substantially liquid infectious waste streams and methods of treating such waste streams are disclosed. The modular waste disinfection system includes a metal ion generation chamber for introducing metal ions into the waste material; an oxidant generation chamber in fluid flow communication with the metal ion generation chamber for disinfection of the waste material with an oxidizing agent; and a chelation chamber in fluid flow communication with the oxidant generation chamber for deactivation of metal ions in the waste material, wherein the waste is discharged to a sanitary sewer after disinfection.

10 Claims, 4 Drawing Sheets

U.S. PATENT DOCUMENTS

| | | | |
|---|---|---|---|
| 5,149,354 | A | 9/1992 | Delaney |
| 5,228,964 | A | 7/1993 | Middleby |
| 5,324,434 | A | 6/1994 | Oikawa et al. |
| 5,346,627 | A | 9/1994 | Siefert et al. |
| 5,364,512 | A | 11/1994 | Earl |
| 5,387,350 | A * | 2/1995 | Mason ................ 210/754 |
| 5,454,953 | A | 10/1995 | Waibel |
| 5,476,579 | A | 12/1995 | Choi et al. |
| 5,492,633 | A | 2/1996 | Moniwa et al. |
| 5,543,040 | A | 8/1996 | Fite, Jr. et al. |
| 5,688,981 | A * | 11/1997 | Nonomura ............. 556/116 |
| 5,753,100 | A | 5/1998 | Lumsden |
| 5,759,384 | A | 6/1998 | Silveri |
| 5,772,896 | A | 6/1998 | Denkewicz, Jr. et al. |
| 5,783,090 | A | 7/1998 | Gleen |
| 5,820,541 | A * | 10/1998 | Berlanga Barrera ...... 588/249.5 |
| 5,858,246 | A | 1/1999 | Rafter et al. |
| 5,858,256 | A | 1/1999 | Minne et al. |
| 5,885,426 | A | 3/1999 | Silveri |
| 5,938,900 | A | 8/1999 | Reynolds |
| 5,944,973 | A | 8/1999 | Hall |
| 5,958,252 | A | 9/1999 | Shades |
| 6,017,461 | A | 1/2000 | Garvey et al. |
| 6,093,422 | A | 7/2000 | Denkewicz, Jr. et al. |
| 6,113,779 | A | 9/2000 | Snee |
| 6,126,830 | A * | 10/2000 | Marshall ................ 210/627 |
| 6,149,821 | A * | 11/2000 | Rounds et al. ........... 210/754 |
| 6,197,814 | B1 * | 3/2001 | Arata ................ 514/495 |
| 6,210,078 | B1 | 4/2001 | Redwine et al. |
| 6,270,650 | B1 | 8/2001 | Kazi et al. |
| 6,287,450 | B1 | 9/2001 | Hradil |
| 6,346,627 | B1 | 2/2002 | Liotta et al. |
| 6,358,395 | B1 | 3/2002 | Schorzman et al. |
| 6,495,052 | B1 | 12/2002 | Miyamoto et al. |
| 6,514,406 | B1 | 2/2003 | Katehis |
| 6,521,131 | B1 | 2/2003 | Hamilton et al. |
| 6,746,593 | B2 * | 6/2004 | Herbst ................ 205/757 |
| 6,780,306 | B2 | 8/2004 | Schlager et al. |
| 7,056,061 | B2 | 6/2006 | Kukor et al. |
| 7,198,680 | B1 * | 4/2007 | Dooley et al. ........... 134/26 |
| 7,238,287 | B2 * | 7/2007 | Kulperger ............... 210/632 |
| 7,387,719 | B2 * | 6/2008 | Carson et al. ............ 205/688 |
| 7,691,251 | B2 * | 4/2010 | Carson et al. ............ 205/688 |
| 2002/0144958 | A1 | 10/2002 | Sherman |
| 2002/0155044 | A1 | 10/2002 | Ciampi et al. |
| 2002/0157962 | A1 | 10/2002 | Robey et al. |
| 2003/0132172 | A1 | 7/2003 | Hayes |
| 2005/0034978 | A1 | 2/2005 | Kazi et al. |
| 2006/0000784 | A1 | 1/2006 | Khudenko |
| 2006/0043011 | A1 | 3/2006 | King et al. |
| 2006/0125396 | A1 | 6/2006 | Han et al. |

OTHER PUBLICATIONS

I.B. Romans, Silver Compounds, Disinfection, Sterilization, and Preservation, 1968, Chapter 28, 469-474, Lea & Febiger, Philadelphia.

M.T. Yahya et al., Disinfection of Bacteria In Water Systems by Using Electrolytically Generated Copper: Silver & Reduced Levels of Free Chlorine, Canadian Journal Of Microbiology, 1990, 109-116, vol. 36.

J. A. Spardo et al., Antibacterial Effects of Silver Electrodes with Weak Direct Current, Antimicrobial Agents And Chemotherapy, Nov. 1974, 637-642, vol. 6, No. 5.

Robert Niven, Investigation of Silver Electrochemistry Water Disinfection Applications, CIVE 651: Principles of Water and Wastewater Treatment, McGill University, Apr. 13, 2005.

H. Akiyama, Prophylaxis of Indwelling Urethral Catheter Infection: Clinical Experience with A Modified Foley Catheter And Drainage System, The Journal of Urology, 1979, 40-42, vol. 121.

Charles F. Mckhann, M.D. et al., Oligodynamic Action of Metallic Elements and of Metal Alloys on Certain Bacteria and Viruses, Dec. 1985, 95-101, vol. 182(1).

F. X. Abad et al., Disinfection of Human Enteric Viruses in Water by Copper and Silver in Combination with Low Levels of Chlorine, Applied And Environmental Microbiology, Jul. 1994, 2377-2383, vol. 60, No. 7.

John Apsley et al., Nanotechnology's Latest Oncolytic Agent: Silver, Cancer, & Infection Associations, Townsend Letter for Doctors and Patients, May 2006.

Leonard Zimmerman, Toxicity of Copper and Ascorbic Acid to Serratia Marcescens, Journal of Bacteriology, Apr. 1966, 1537-1542, vol. 91, No. 4.

Oligodynamic Ag: The Active Ingredient in Sovereign Silver and Argentyn 23, Natural-Immunogenics Corp.

Dual Sanitation with Copper Silver Ion, Ideal Distributors Limited, 2007, 1-4.

H.T. Michels et al., Copper Alloys for Human Infectious Disease Control, Materials Science and Technology Conference, Sep. 25-28, 2005, Pittsburg, PA.

J. O. Noyce et al., Use of Copper Cast Alloys to Control *Escherichia coli* O157 Cross-Contamination During Food Processing, Applied and Environmental Microbiology, Jun. 2006, 4239-4244, vol. 72, No. 6.

Tests Show Silver Best "Swimming Pool" Water Purifier, The Silver Institute Letter, May 1975, vol. VI, No. 11.

Silver, Nature's Water Purifier, www.doulton.ca/silver.html., Feb. 27, 1997, 1-6.

John G. Dean et al., Heavy Metals from Waste Water, Environmental Science & Technology, Jun. 1972, 519-522, vol. 6, No. 6.

J. M. Cassells et al., Efficacy of a Combined System of Copper and Silver and Free Chlorine for Inactivation of Naegleria Fowleri Amoebas in Water, Water Science and Technology, 1995, 119-122, vol. 31, No. 5-6.

R. R. Khaydarov et al., Water Disinfection Using Silver and Copper Ions and Colloidal Gold, Modern Tools and Methods of Water Treatment for Improving Living Standards, 2005, 159-166, Netherlands.

X. Y. Li et al., Electrochemical Wastewater Disinfection: Identification of Its Principal Germicidal Actions, Journal of Environmental Engineering, Oct. 2004, 1217-1221.

X. Y. Li et al., Electrochemical Disinfection of Saline Wastewater Effluent, Journal of Environmental Engineering, Aug. 2002, 697-704.

Q. L. Feng et al., A Mechanistic Study of the Antibacterial Effect of Silver Ions on *Escherichia coli* and Staphylococcus Aureus, Journal of Biomedical Materials, 2000, 662-668, vol. 52.

Lee K. Landeen, Efficacy of Copper and Silver ions and Reduced Levels of Free Chlorine in Inactivation of Legionella Pneumophila, Applied and Environmental Microbiology, Dec. 1989, 3045-3050, vol. 55, No. 12.

Janet E. Stout, Experiences of the First 16 Hospitals Using Copper-Silver Ionization for Legionella Control: Implications for the Evaluation of Other Disinfection Modalities, Infection Control and Hospital Epidemiology, Aug. 2003, 1-6, vol. 24, No. 8.

Andrew A. Marino, Eletrochemical Properties of Silver-Nylon Fabrics, Journal of the Electrochemical Society, Electrochemical Science and Technology, Jan. 1985, 68-72, vol. 132, No. 1.

C. P. Davis, Iontophoretic Killing of *Escherichia coli* in Static Fluid and in a Model Catheter System, Journal of clinical Microbiology, May 1982, 891-894, vol. 15, No. 5.

J. M. Cassells et al., Efficacy of a Combined System of Copper and Silver and Free Chlorine for Inactivation of Naegleria Fowleri Amoebas in Water, Water Science and Technology, 1995, 119-122, vol. 31, No. 5-6.

R. R. Khaydarov et al., Water Disinfection Using Silver and Copper Ions and Colloidal Gold, Modern Tools and Methods of Water Treatment for Improving Living Standards, 2005, 159-166, Netherlands.

X. Y. Li et al., Electrochemical Wastewater Disinfection: Identification of Its Principal Germicidal Actions, Journal of Environmental Engineering, Oct. 2004, 1217-1221.

X. Y. Li et al., Electrochemical Disinfection of Saline Wastewater Effluent, Journal of Environmental Engineering, Aug. 2002, 697-704.

Q. L. Feng et al., A Mechanistic Study of the Antibacterial Effect of Silver Ions on *Escherichia coli* and Staphylococcus Aureus, Journal of Biomedical Materials, 2000, 662-668, vol. 52.

* cited by examiner

IN-LINE WASTE DISINFECTION METHOD

TECHNICAL FIELD

The disclosure relates to an in-line waste and/or modular disinfection unit intended to provide for treatment and/or disinfection of liquid infectious wastes, including medical, domestic, scientific, mortuary, or commercial wastes, before flowing the waste stream to a sanitary sewer drain or directly to the environment.

BACKGROUND AND SUMMARY

There is growing concern that biological infectious waste streams from hospitals, slaughter houses, and other sources that may contain biologically hazardous or toxic components are not adequately treated before discharging such waste streams to sanitary sewer systems or directly to the environment. Large municipal treatment facilities may not adequately be configured for high concentrations of biological materials originating in hospitals and other sources. Accordingly, there is a need for improved systems and methods for treating waste streams before the streams are discharged into a sanitary sewer system or directly to the environment. There is also a need for modular systems that may be readily deployed into an existing sanitary sewer system at the source of the waste stream thereby reducing the degree of infectivity of the material a municipal system must treat.

In view of the foregoing and other needs, an exemplary embodiment of the disclosure provides a modular waste disinfection system for substantially liquid infectious waste streams and methods of treating such waste streams. The modular waste disinfection system may include a metal ion generation chamber for introducing metal ions into the waste material; an oxidant generation chamber in fluid flow communication with the metal ion generation chamber for disinfection of the waste material with an oxidizing agent; and a chelation chamber in fluid flow communication with the oxidant generation chamber for deactivation of metal ions in the waste material.

Another exemplary embodiment of the disclosure provides a method of treating a sanitary sewer waste material to provide a treated waste stream. The method may include flowing a waste stream from a sanitary sewer drain into a modular waste disinfection system. The modular waste disinfection system may include a metal ion generation chamber for introducing metal ions into the waste material to partially disinfect the waste material; an oxidant generation chamber in fluid flow communication with the metal ion generation chamber for disinfection of the waste material with an oxidizing agent; and a chelation chamber in fluid flow communication with the oxidant generation chamber for deactivation of metal ions and oxidation chemicals in the waste material.

According to the method, the waste stream may be macerated to a predetermined particle size and may be contacted with a film inhibitor and/or a foam inhibitor in the maceration chamber. Metal ions may be generated in situ in the metal ion generation chamber for contact with the waste stream from the maceration chamber to disinfect the waste stream. The waste stream may be oxidized in the oxidant generation chamber by oxidants generated in situ, in order to eliminate any biological activity in the waste stream. The metal ions in the waste stream may then be chelated in the chelation chamber in order to sequester and deactivate any remaining metal ions and oxidizing chemicals present in the waste stream before discharging the treated waste stream into a sanitary sewer or directly to the environment.

An advantage of the system and methods described herein is that the system combines at least two disinfection techniques in a single unit thereby increasing the effectiveness of waste stream disinfection over the use of a single disinfection technique. Unlike conventional systems, the active disinfection ingredients are deactivated prior to the waste stream being discharged from the disinfection unit so that the disinfection ingredients and waste stream may be discharged to the sanitary sewer system or directly to the environment without removing the disinfection ingredients from the waste stream. Because of the modular components of the system, the system may be configured as a mobile, or portable, stand-alone unit or may be provided in a substantially fixed non-portable installation that may be inserted between a waste material source and a final disposition of the waste material. The waste treatment system may also be combined and/or integral with a waste collection system or may be configured as a stand-alone system for discharge directly to the environment.

Additional objects and advantages of the disclosure are set forth in part in the description which follows, and/or may be learned by practice of the disclosure. The objects and advantages of the disclosure may also be realized and attained by means of the elements and combinations particularly pointed out in the appended claims.

It is to be understood that both the foregoing general description and the following detailed description are exemplary and explanatory only and are not restrictive of the disclosure, as claimed.

BRIEF DESCRIPTION OF THE DRAWINGS

Further advantages of the exemplary embodiments may become apparent by reference to the detailed description of the exemplary embodiments when considered in conjunction with the following drawings illustrating one or more non-limiting aspects thereof, wherein like reference characters designate like or similar elements throughout the several drawings as follows.

DESCRIPTION OF THE EXEMPLARY EMBODIMENTS

Figure 1:
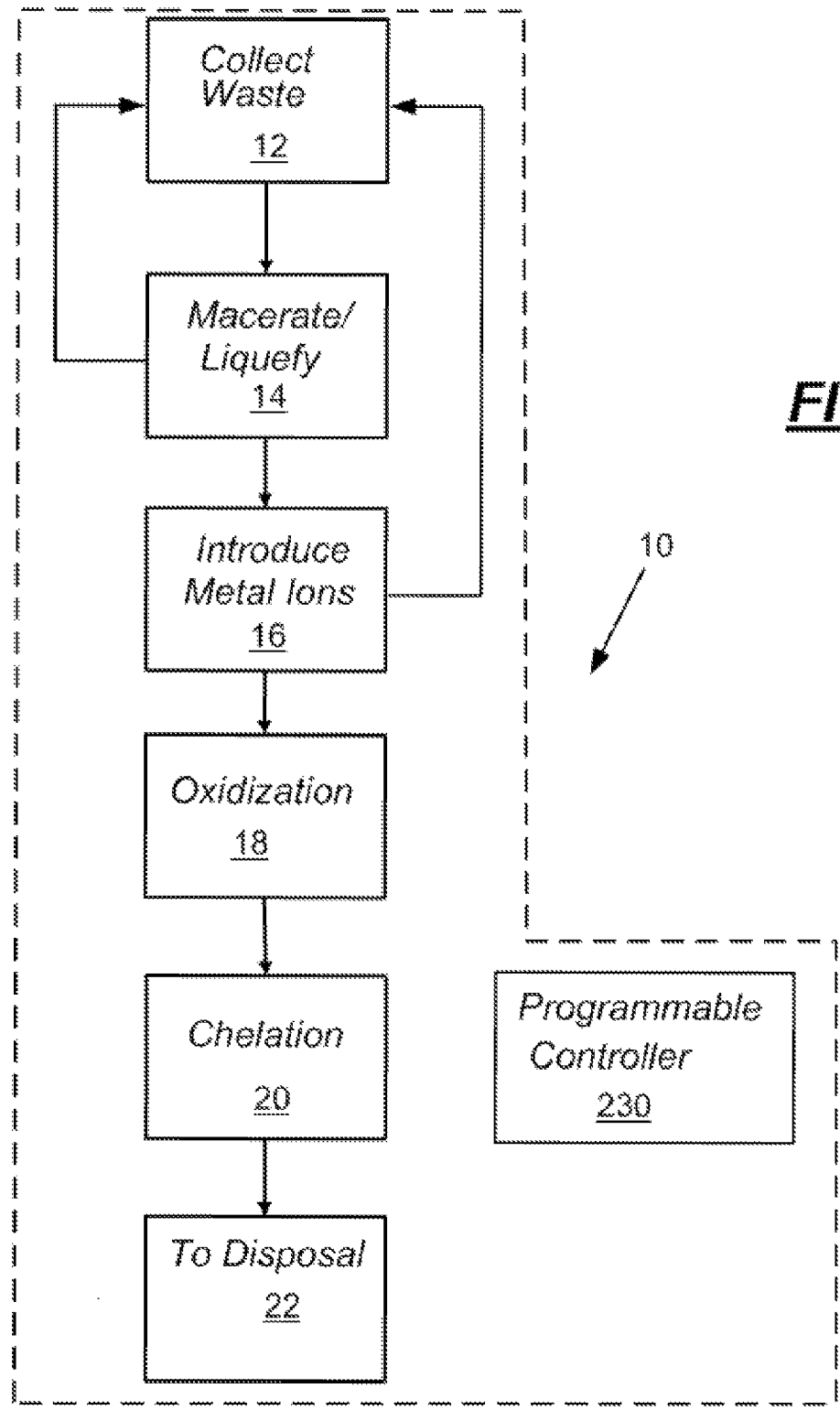
FIG. 1 is a block flow diagram of one embodiment of a method of the present disclosure.

As described in more detail below, embodiments of the present disclosure may provide systems and methods for disinfecting substantially liquid infectious waste streams before discharging the waste streams to a sanitary sewer system or directly to the environment. The deactivation or destruction of infectious agents, such as viruses, bacteria, protists, fungi, algae, prions, or other infectious organic matter, through embodiments of the present disclosure may be herein referred to as "disinfection" or "biocidal activity." The systems and methods may be adaptable to being portable or to being permanently attached to existing sanitary sewer drains. Each system may be substantially self-contained so that fluid discharged from the system may be suitable to flow into an existing sanitary sewer or directly to the environment without further disinfection.

The systems and methods of the present disclosure may generate reactive disinfection agents in situ during the course of operation. Waste streams may be treated with a synergistic combination of metal ions and oxidants, such as hypochlorites, peroxides, or hydroxyl ions. However, it is not desirable to discharge metal ions and oxidants into the sewer system. Therefore, the waste streams may be further treated to ensure deactivation of the reactive agents and allow for discharge of the waste stream through a sewer system or directly to the environment.

The oxidants may be generated electrolytically in situ from water having minimal amounts of common salt (sodium chloride) present or from salts existing in organic tissues that may be present in the waste. The metal ions may likewise be generated in situ via redox reactions when electrodes comprising the appropriate metals are subjected to an electrical current of suitable polarity, voltage, and time duration. The ability to generate both metallic ions and reactive nonmetallic compounds in situ by electrolytic redox reactions provides a key disinfecting technique, generating the biocidal species on the spot as they are needed. Any active disinfecting agents not chemically deactivated as a result of the disinfection process may then be bound and deactivated by subsequent processing at the end of the disinfection cycle.

Unlike conventional disinfection systems, the system described herein may bind and deactivate the metal ions used for disinfection before discharge of a treated fluid stream to the sewer system, rather than removing the metal ions by precipitation or other reaction mechanism. The presently disclosed system may charge a sufficient quantity of a chelating agent, such as EDTA or citric acid, to a chelation chamber, which may bind the metal ions and inactivate them. Chelation may also serve to bind unreacted oxidants that may be present in the stream. This binding technique is similar to the treatment used by physicians to treat ingestion of toxic metals for excretion from the body, and may allow for the chelated metals to be safely discharged into the sewer system or directly to the environment.

The present disclosure may also exploit the powerful biocidal properties of oxidizing agents, such as hypochlorites and peroxides. The aforementioned and related chemicals, generally known as oxidants, are well known and established as highly effective microbicides.

Hypochlorites may also display effectiveness against viruses by virtue of an ability to attack and denature proteins. This feature makes them effective against viruses which may be either coated with an external protein coat, or uncoated. The oxidizing agents made and used in the system for their biocidal activity may also be deactivated or neutralized in situ by spontaneous reactions with organic compounds in the waste, without the need to remove these chemicals from the treated fluid stream.

While both metal ions and oxidizing agents are known to be effective biocidal agents individually, the combination of metal ions and oxidants in a single system may provide a synergistically improved effectiveness in biocidal activity that may be about 100,000 times greater than the disinfectant effectiveness of either the metal ions or the oxidants alone.

With reference to FIG. 1, one embodiment of a method of the present disclosure provides a system 10 that includes a series of continuous, in-line processes for the disinfection of a substantially liquid infectious waste stream, with each process stage further described in more detail below. Each process stage may herein be represented as an individual physical chamber in order to provide a clearer understanding of the in-line process concept. However, the present disclosure is not limited to individual chambers for each process stage, as in an alternative embodiment discussed below. The presently described process stages may be implemented either in individual chambers to simplify control or be combined in common chambers to achieve an optimum footprint for the physical dimensions and cost/benefit to the unit design configuration.

Infectious waste is first collected in a waste collection step 12, where water may be added if necessary to ensure that the waste material is substantially liquid or in substantially liquid form for further treatment. Accordingly, the waste material may also be macerated in a maceration step 14. The maceration step 14 may ensure a homogenous particulate size for any organic matter that may be present in the substantially liquid waste material. The term "substantially liquid" means that any solids present in the waste material remain substantially suspended in a liquid phase for flow through the system 10.

If the particulate size of any organic matter present is too large for the waste to be processed in the next process step, the waste material may be recycled for further maceration in the maceration step 14. Next, metal ions may be introduced into the waste material in a metal ion generation step 16, where electrolysis of a sacrificial electrode may generate oligodynamic concentrations of metal ions in situ. The waste material may remain at or be recirculated through this stage for a period of several minutes, in order to infuse an adequate concentration of metal ions into the waste material and/or to allow sufficient time for the metal ions to at least partially disinfect the waste material.

In the next step of the process, the waste material may be oxidized in an oxidation step 18, wherein reactive oxidizing ions, for example hypochlorite, may be electrolytically generated in situ. The waste material may be treated with oxidizing ions for a period of several minutes, in order to allow sufficient time to produce adequate concentrations of oxidizing ions in the waste material and/or for the oxidants to at least partially disinfect the waste material. There may be residual metal ions from the metal ion generation step 16 present during the oxidation step 18.

After the oxidation step 18, the waste material may then be passed to a chelation step 20, wherein any metal ions remaining in the waste material may be bound to a chelating agent, thereby removing such ions from the treated waste material. The waste material may remain at this stage for a period of several minutes, in order to allow sufficient time for the chelating agent to sequester the metal ions. Chelation may also serve to bind unreacted oxidants that may be present in the stream. Finally, the waste material may be discharged or disposed of through a waste disposal step 22 to a sanitary sewer system or directly to the environment.

Figure 2:
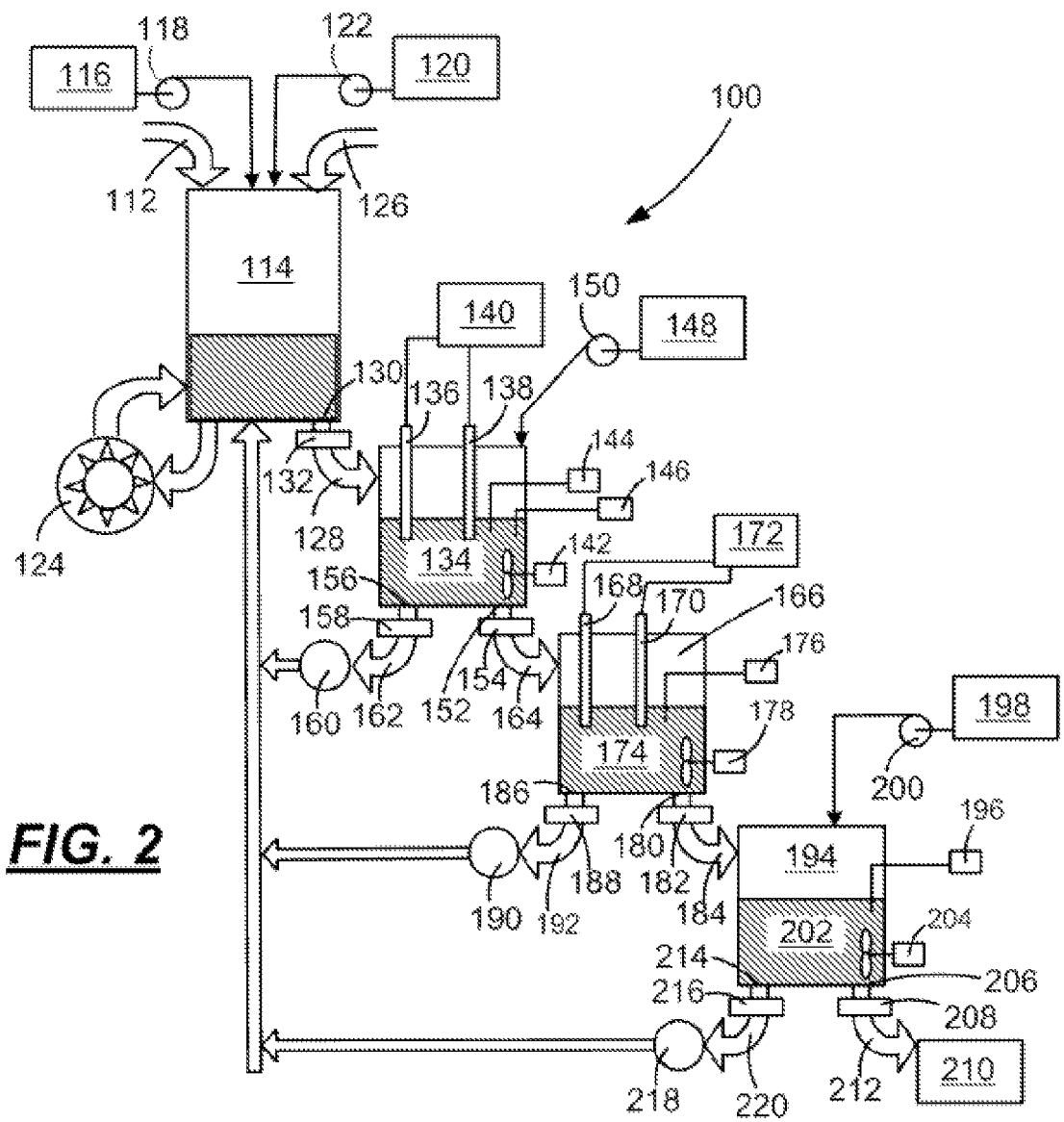
FIG. 2 is a schematic representation of one non-limiting example of an embodiment of a system of the present disclosure.

In order to further illustrate aspects of exemplary embodiments of the disclosure, reference is now made to FIG. 2. FIG. 2 is a non-limiting, schematic illustration of a modular system 100 including the process steps described above with reference to FIG. 1.

As shown in FIG. 2, a substantially liquid infectious waste stream 112 comprising biological waste may be fed into a holding chamber 114. A film inhibitor reservoir 116 including a film inhibitor dosing pump 118, and a foam suppressant reservoir 120 including a foam suppressant dosing pump 122 may be associated with the holding chamber 114 for feeding a film inhibitor and/or a foam suppressant into the holding chamber. A macerator 124 may also be associated with the holding chamber 114, wherein the waste material in the holding chamber 114 may be mechanically macerated to reduce the size of any solid material in the holding chamber and to combine the waste with water or other aqueous solution that may be introduced to the holding chamber 114, as needed, via an additional input line 126. The holding chamber 114 may be constructed of copper or copper alloy to provide an inherent bactericidal action thereby suppressing undesirable bacterial growth. Similar bactericidal action may be obtained by copper plating or use of a copper or copper alloy floorplate in the holding chamber 114.

The metered dose of a film inhibitor, such as sodium lauryl sulfate ("SLS") is believed to perform two critical functions. First, the film inhibitor may initiate a chemical attack to begin breaking down and denaturing both lipid and protein complexes present in the waste. Second, the film inhibitor's inherent detergency properties may enable the holding chamber 114 to remain "self-cleaning." As an additional feature, SLS is also well known as a disinfecting agent, and it may contribute to the overall synergistic disinfectant effect of the present system 100. An amount of SLS that may be metered into the holding chamber 114 may range from about 0.1 to about 10.0 percent by volume.

The foam suppressant, such as a silicone-based antifoam agent, may further ensure that air bubble formation is reduced during maceration cycles, so that air entrapment does not inhibit the operating efficacy of the reactive disinfectant species generated in the subsequent disinfection chambers. An amount of foam suppressant that may be used to suppress air entrapment in the holding chamber 114 may range from about 0.05 to about 1.0 percent by volume.

The holding chamber 114 may employ one or more macerators 124 for chopping or mixing material within the chamber 114 in order to macerate and mix the incoming waste stream 112 with the water and the solution of film inhibitor and foam suppressant. Macerating the waste stream 112 may also extend the time of contact between the waste stream 112 and metal ions or oxidizing chemicals in the system 100. The initial maceration may aid to break down organic solids in the waste stream 112 to a homogenized rough particle size and may introduce a water or other aqueous solution carrier necessary to establish a waste stream 128 flow into a subsequent chamber.

A suitable particle size exiting the holding chamber 114 may be less than about 0.5 millimeters in diameter and typically less than 0.3 millimeters in diameter after maceration. For example, the maximum particle size exiting from the macerator 124 may range from about 0.25 to about 0.5 millimeters in diameter. The initial particle size of particles entering the macerator may range from about 5 to about 10 millimeters in diameter. The term "diameter" is used to signify an average cross-sectional dimension of particles based on the largest cross-section of the particles in the waste stream 112 and is not intended to indicate that the particles are necessarily circular or spherical.

The holding chamber 114 may further comprise a fluid exit port 130 comprising a unidirectional valve 132 and/or a pump for allowing a sufficiently homogenized waste stream 128 to enter a metal ion generation chamber 134 that may be in fluid flow communication with the holding chamber 114.

The metal ion generation chamber 134 contains at least one pair of electrodes 136, 138 that may be electrically connected to a power supply 140. The electrodes 136, 138 may comprise one or more metals, including aluminum, silver, copper, iron, bismuth, gold, or zinc. The metal composition of the electrodes 136, 138 may provide a source for the electrolytic generation of corresponding metal ions.

The power supply 140 may provide electrical energy for the electrodes 136, 138. Application of electrical energy to the electrodes 136, 138 may cause metal ions to be liberated from the electrodes via one or more redox reactions. The liberated metal ions may then become dissolved in the waste mixture particulate suspension in the metal ion chamber 134 so that the ions may provide disinfecting activity to the waste. The voltage and current applied to the electrodes 136, 138 may be externally regulated in order to exercise control over the concentration of metal ions that may be dissolved in the waste suspension in the chamber 134.

Multiple pairs of electrodes 136, 138, each electrode comprising one or more metal compositions and having an appropriate voltage and current flow, may be used to introduce various concentrations of one or more metal ions into the waste mixture suspension. The metal ion generation chamber 134 may itself be used as one of the electrodes.

The dissolved metal ions may act oligodynamically within the waste suspension to deactivate or destroy bacterial, protist, fungal, algal, prion, and viral infectious agents present within the waste. It is believed that a total metal ion concentration of at least several parts per million is suitable for disinfection purposes.

In one embodiment, both silver and copper ions may be produced. It is believed that a concentration of copper ions that is much greater than a concentration of silver ions is particularly suitable for disinfection of waste liquids. Although a concentration ratio of 10:1 Cu to Ag has been found to be highly effective, other ratios may prove to be suitable for this application. Accordingly, ions of different metals may be produced at different concentration levels in order to provide a suitable total dissolved metal ion concentration. In one embodiment, a suitable copper ion concentration may range from about 100 ppm to about 1000 ppm, with a further suitable example being about 400 ppm of copper ions. Likewise, suitable silver ion concentration may range from about 10 ppm to about 100 ppm, with a further suitable example being about 40 ppm of silver ions. A suitable total metal ion concentration for disinfection may range from about 110 ppm to about 1100 ppm. As a further example, a suitable total metal ion concentration may range from about 200 ppm to about 800 ppm, and as another suitable example a total metal ion concentration may range from about 300 ppm to about 600 ppm.

A metal ion exposure time ranging from about 1 to about 30 minutes may be suitable to provide disinfection to the waste stream, with a further suitable example ranging from about 5 to about 10 minutes of exposure time. Particularly resistant wastes may require additional time or higher concentration of the metal ions. Variations in operation may be accommodated by process control using a programmable controller as part of the system 100.

The electrodes 136, 138 used to produce the metal ions may be pure metals in which multiple pairs of electrodes 136, 138 may be used and voltages and currents to each electrode 136, 138 pair regulated independently in order to control the various metal ion concentrations. The electrodes 136, 138 may also be composed of a mixture of more than one metal, such as a metal alloy, in order to control the concentration of each ion in solution. Each of the electrodes in the pair of electrodes 136, 138 may comprise a distinct and independent composition.

The electrodes 136, 138 may be fabricated employing powder metallurgy. A further embodiment using copper powder and silver or silver-alloy "solder" may be employed as a binder. The powdered metal electrodes 136, 138 may be fabricated such that the concentration of exposed metals such as copper or silver could be carefully controlled to produce the desired concentration ratio of metal ions. Additionally, the composition of each electrode 136 or 138 and its corresponding ionic contribution may be controlled through particle size and amount of each phase, primary metal and "binder"

present in the powder molded electrode 136 or 138. For example, large spherical grains of copper may be pressed with silver solder powder and sintered to form an electrode 136 with higher surface concentrations of copper. Studies have shown that a combination of copper and silver ions wherein the concentration of copper ions is much higher than the concentration of silver ions may be very effective in disinfecting liquid containing biological hazards.

In a further embodiment of the present disclosure, one or more electrodes 136, 138 may be integrated into a mixing device or mixing pump 142 in which the various vanes or other portions of the mixing device may also act as an electrode. In an alternative embodiment, a mixing device 142 may comprise an electrode and may be used in combination with electrodes 136, 138.

The metal ion generation chamber 134 may further comprise a fluid level meter 144, a conductivity meter 146, a saline reservoir 148 and a saline dosing pump 150. The metal ion generation chamber 134 may also comprise a fluid exit port 152 comprising a directionally restrictive fluid flow valve 154 and/or pump. Hence, the metal ion generation chamber 134 may be in fluid flow communication with at least one subsequent treatment chamber. A second fluid exit port 156 comprising a recycling valve 158 and/or pump 160 may allow at least a portion 162 of the waste treated in the metal ion generation chamber 134 to be returned to the holding chamber 114 so that the portion 162 of waste may be recycled through the system 100 and further disinfected.

The metal ion treated waste stream 164 may then be passed into an oxidant generation chamber 166. The oxidant generation chamber 166 may comprise a set of electrodes 168, 170, each composed of a material selected from carbon, titanium, stainless steel, and relatively inert materials. The electrodes 168, 170 are in electrical connection with a power supply 172. Application of electric current to the electrodes may cause hypochlorite or other reactive, disinfectant, oxidant species to be generated and to flow through, and dissolve in, the waste mixture particulate suspension 174 present within the oxidant generation chamber 166.

A suitable oxidant concentration may range from about 0.10 ppm to about 10 ppm, with a further example of a suitable oxidant concentration ranging from about 1 ppm to about 5 ppm. An oxidant exposure time ranging from about 1 to about 20 minutes may be suitable to provide disinfection to the waste suspension 174, with a further suitable example being from about 5 to about 10 minutes of exposure time. Particularly resistant wastes may require additional time or higher concentration of the metal ions. Variations in the oxidant concentration be accommodated by process control using a programmable controller.

The oxidant generation chamber 166 may also comprise a fluid level sensor 176 and a mixer 178. A fluid exit port 180 comprising a directionally restrictive fluid flow valve 182 and/or pump may allow oxidant treated waste 184 to be passed to a subsequent chamber in fluid flow communication with the oxidant generation chamber 166. A second fluid exit port 186 comprising a recycling valve 188 and/or pump 190 may allow at least a portion 192 of the waste suspension 174 to be passed to the holding chamber 114 or to a previous chamber so that the portion 192 of waste suspension 174 may be recycled through the system 100 and further disinfected.

The oxidant treated waste 184 may then be passed into a chelation chamber 194 comprising a fluid level sensor 196, a chelating agent reservoir 198, and a chelating agent dosing pump 200. A quantity of chelating agent may be provided to the waste material 202 in the chelation chamber 194 from the reservoir 198 by the dosing pump 200 in order to facilitate removal of the metal ions. A mixing device 204 may provide continuous circulation and contact of the waste 202 with the chelation agent in the chelating chamber 194. The waste 202 may be processed in a timed chelation cycle that may allow the metal ions to be bound chemically to the chelating agent and may ensure that the oxidants have fully reacted with any organic materials present in the suspension.

The timed chelation cycle may range in duration from about 1 to about 30 minutes, with another suitable example being from about 5 to about 10 minutes. The amount of chelating agent in the chelation chamber 194 sufficient to chemically bind any metal ions may range from about a molar equivalent of the metal ion concentration to about one and a half times a molar equivalent of the metal ion concentration. Typically, the amount of chelating agent will be about a molar equivalent of the metal ion concentration in the waste 202.

A suitable chelating agent may be selected from EDTA, citric acid, sodium citrate, acetylacetone, ethylenediamine, diethylenetriamine, tetramethylethylenediamine, 1,2-ethanediol, 2,3-dimercaptopropanol, porphyrin, gluconic acid, or similar compounds.

Following completion of the timed chelation cycle, the treated waste 202 may be discharged through a fluid exit port 206, comprising a unidirectional valve 208 and/or pump, into a sanitary sewer system 210 in a disinfected and chemically inert state by either pumping or gravity flow into a sanitary sewer drain. A sewer discharge connection 212 may serve to maintain fluid flow communication between the disinfection system and the sewer system. The chelation chamber 194 may further comprise a second fluid exit port 214 comprising a recycling valve 216 and/or pump 218 that may allow at least a portion 220 of the waste material 202 to be returned to the holding chamber 114 or a previous chamber so that the portion of waste 220 may be recycled through the system 100 and further disinfected.

Embodiments of the present disclosure may also comprise a programmable controller 230 (FIG. 1) capable of interfacing with the fluid level sensors 144, 176 and 196, conductivity sensor 146, and other sensors that may be present in order to coordinate the activities of dosing pumps 118, 122, 150 and 200, valves 132, 154, 158, 182, 188, 208 and 216, pumps 160, 190, and 218 and macerator 124, to estimate the amount of waste being processed, to control the electrode voltage and currents responsible for producing the active disinfecting agents, and to control the time intervals for each stage of waste processing. The controller 230 may also estimate the amount of chelating agent required in the chelation chamber based on sensor feedback.

Figure 3:
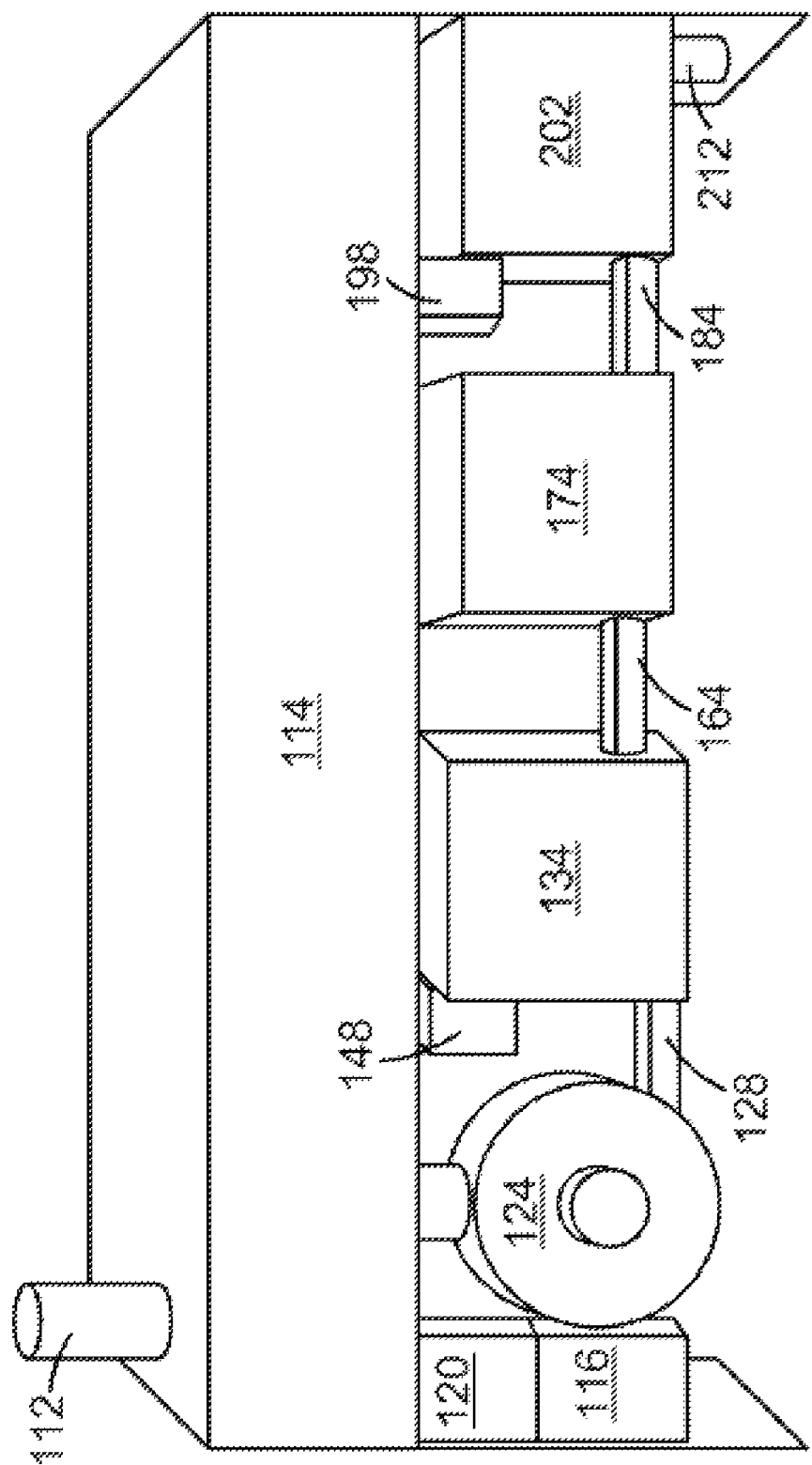
FIG. 3 is a perspective, cut-away view, not to scale, of a substantially linear waste disinfection unit according to an embodiment of the disclosure.
Figure 4:
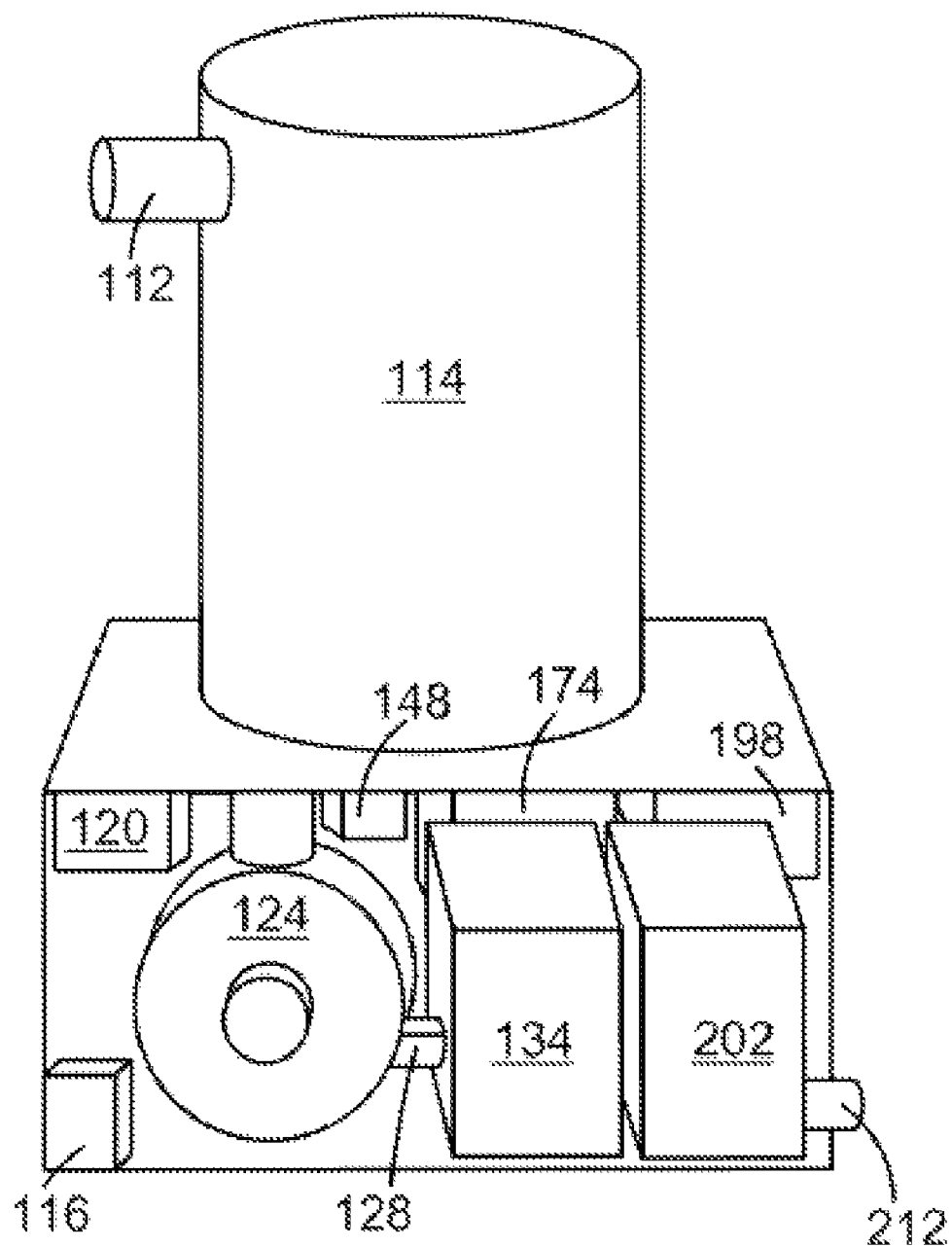
FIG. 4 is a perspective, cut-away view, not to scale, of a substantially vertical waste disinfection unit according to another embodiment of the disclosure.

Compact arrangements of the components of the system 100 are illustrated, for example in FIGS. 3 and 4. FIG. 3 is a substantially linear arrangement of the components of the system 100 described above. In the linear arrangement depicted in FIG. 3, the overall height of the system 100 is minimized so that the system may be installed under an existing sink. Accordingly, the dimensions of such a system may range from about 24 inches to about 36 inches in length, from about 12 inches to about 16 inches in width, and from about 15 inches to about 20 inches in height.

An alternative arrangement of the components of the system is illustrated in FIG. 4. FIG. 4 depicts a substantially vertical arrangement of the components of the system. The system depicted in FIG. 4 may have overall dimensions ranging from about 24 inches to about 30 inches square, and from about 24 inches to about 36 inches in height. Other arrangements of the components of the system may be possible so that a reduced height and a reduced length are provided.

However, it is desirable that the components be arranged in a compact manner so that the system 100 is relatively compact and/or portable.

The system 100 may be particularly adapted to treating waste liquid streams 116 containing bacteria, surgical waste, biological or biologically toxic materials. Such materials may include, but are not limited to, dairy shed waste, fowl waste, milk processing plant waste, food processing wastes, waste from the wine and brewery industries, food waste, shipboard waste, sewage, medical waste, and the like.

In a further embodiment, an ability to reverse the direction of electrical current flow between a pair of electrodes may be desirable to prevent and remove a build-up of residual mineral scale which may form as a by-product of the electrolytic reactions used to generate the disinfecting agents. Such scale may impede the generation of further disinfecting agents over time. The ability to remove mineral scale by a reversal of electrical current flow may allow the electrodes to have a longer effective disinfectant generation lifetime, and may provide an economic benefit by decreasing the frequency of electrode replacement.

In embodiments of the present disclosure, replaceable electrodes and replaceable cartridges or refillable reservoirs of chelating agents, film inhibitors, foam suppressants, and saline solution may be provided. In one embodiment, the cartridges or reservoirs and the electrodes are accessible from the exterior of the system in order to facilitate ease of refilling or replacement by the user.

The individual process stages, discussed above as occurring in a separate chamber for each stage, are not limited to such an embodiment. Multiple stages may occur concurrently in a single physical chamber. For example, in an alternative embodiment, the metal ion generation chamber 134 and the oxidant generation chamber 174 may be combined into a single electrochemical disinfection chamber, where the simultaneous generation of metal ions and oxidizing agents in situ may provide a greater synergistic disinfectant activity, and a more efficient cost-effective disinfection process.

A trimming electrode (not shown) may be added to the combined chamber in order to ensure that the current level may be adjusted to provide for suitable concentration levels of the active metal ions and oxidants. The trimming electrode may be in electrical communication with the controller 230.

As used throughout the specification and claims, "a" and/or "an" may refer to one or more than one. Unless otherwise indicated, all numbers expressing quantities of ingredients, properties such as molecular weight, percent, ratio, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Other embodiments of the present disclosure will be apparent to those skilled in the art from consideration of the specification and practice of the embodiments disclosed herein. Accordingly, the embodiments are not intended to be limited to the specific exemplifications set forth hereinabove. Rather, the foregoing embodiments are within the spirit and scope of the appended claims, including the equivalents thereof available as a matter of law.

The patentees do not intend to dedicate any disclosed embodiments to the public, and to the extent any disclosed modifications or alterations may not literally fall within the scope of the claims, they are considered to be part hereof under the doctrine of equivalents.

What is claimed is:

1. A method of treating a liquid biological waste stream containing suspended solids, and biologically hazardous or toxic waste components comprising the steps of:
    flowing said waste stream containing substantially suspended solid particles into a waste treatment apparatus
    generating metal ions in the waste treatment apparatus for contact with the waste stream containing substantially suspended solid particles to disinfect the waste stream; wherein the metal ions comprise metal ions selected from the group consisting of aluminum, zinc, silver, iron, bismuth, gold, and copper ions
    oxidizing the waste stream in the waste treatment apparatus to eliminate any toxic and biological activity in the waste stream; and
    chelating the waste stream in the waste treatment apparatus to deactivate any metal ions and oxidizing chemicals remaining in the waste stream.

2. The method of claim 1, further comprising contacting the waste stream in the waste treatment apparatus with a lipid/protein complex film inhibitor.

3. The method of claim 2, wherein the lipid/protein complex film inhibitor comprises sodium lauryl sulfate.

4. The method of claim 1, further comprising contacting the waste stream in the waste treatment apparatus with a foam inhibitor.

5. The method of claim 4, wherein the foam inhibitor comprises an antifoam agent.

6. The method of claim 1, wherein the step of oxidizing the waste stream comprises exposing the waste stream to one or more oxidizing agents selected from the group consisting of oxygen, hypochlorites, peroxides, ozone, chloride ions, and chlorine radicals.

7. The method of claim 1, wherein the step of chelating the waste stream comprises exposing the waste stream to one or more chelating compounds selected from the group consisting of EDTA, citric acid, sodium citrate, acetylacetone, ethylenediamine, diethylenetriamine, tetramethylethylenediamine, 1,2-ethanediol, 2,3-dimercaptopropanol, porphyrin, and gluconic acid.

8. The method of claim 1, wherein substantially all biological and toxic waste materials in the waste stream are effectively treated prior to a step of discharging the treated waste stream from the waste treatment apparatus.

9. The method of claim 1, further comprising macerating the waste stream to reduce a particles size of material in the waste stream to form a substantially liquid flowable waste material.

10. The method of claim 1, further comprising recycling the waste stream to the waste treatment apparatus.

* * * * *